United States Patent [19]

Woudstra

[11] 4,437,065

[45] Mar. 13, 1984

[54] ARRANGEMENT FOR MONITORING CATHODICALLY PROTECTED STRUCTURES

[75] Inventor: Gerrit Woudstra, Roden, Netherlands

[73] Assignee: Stamicarbon B.V., Geleen, Netherlands

[21] Appl. No.: 298,520

[22] Filed: Sep. 1, 1981

[30] Foreign Application Priority Data

Sep. 12, 1980 [NL] Netherlands ............... 8005149

[51] Int. Cl.³ ................................. G01N 27/42
[52] U.S. Cl. ........................... 324/425; 324/65 CR; 324/72; 324/71.1
[58] Field of Search ............... 324/425, 71.1, 65 CR, 324/72, 54, 348, 357, 140, 433, 443

[56] References Cited

U.S. PATENT DOCUMENTS 2,700,501  1/1955  Wang ...................... 324/140 R
4,258,323  3/1981  Andrews et al. ............ 324/348

FOREIGN PATENT DOCUMENTS 54-149011  11/1979  Japan ..................... 324/65 CR

*Primary Examiner*—Michael J. Tokar
*Assistant Examiner*—Kevin D. O'Shea
*Attorney, Agent, or Firm*—Cushman, Darby & Cushman

[57] ABSTRACT

An arrangement for monitoring the potential of a cathodically protected buried metallic structure. The apparatus includes a measuring electrode to be inserted into the soil and electrically coupled to the metallic structure to be measured, a reference electrode placed on or in the soil, and a measuring circuit for measuring the potential difference between the measuring and reference electrodes. The measuring circuit also generates a reference potential to generate a pulse signal having a frequency proportional to the amount by which the measured potential exceeds the reference potential. A counter counts the number of pulses during a measuring cycle that is measured by a timer. A computer computes from timer and counter output data, the average value of the amount by which the measured potential exceeds the reference potential during a measuring cycle.

14 Claims, 3 Drawing Figures

ARRANGEMENT FOR MONITORING CATHODICALLY PROTECTED STRUCTURES

BACKGROUND OF THE INVENTION

The invention relates to a process for monitoring the potential with respect to the soil of a buried metallic structure that is cathodically protected by a DC voltage applied thereto. A measuring electrode is inserted into the soil near the cathodically protected structure. This measuring electrode is electrically connected to the metallic structure and to a measuring circuit for measuring the potential difference between the measuring electrode and a reference electrode situated on or in the soil.

Depending on the type of soil in which a cathodically protected metal structure, such as a steel pipeline, is situated, the potential of the structure with respect to the soil must be lower than $-850$ mV to $-950$ mV in order to prevent corrosion. In order to ensure good operation of the cathodic protection system, one should check this potential regularly.

A known arrangement for monitoring the cathodic protection potential of a buried metallic structure is described in German Patent Application laid open for public inspection No. 2707265 incorporated herein by reference. In that known arrangement the voltage difference between the protected structure and the reference electrode is not measured directly. Direct voltage measurement would yield an inaccurate result because of the voltage drop through the soil caused by the passage either of a current flow due to the applied cathodic protective voltage or by the passage of stray currents derived from nearby electrical installations. When, as indicated, use is made of a measuring electrode connected to the structure, the measuring electrode and the reference electrode can be so positioned with respect to one another that no extraneous voltage drop is produced between them by the passage of current through the soil. For example, a single measuring probe can contain both the measuring electrode and the reference electrode in close proximity to one another. In the measuring probe described in the above-mentioned German patent application No. 2707265, the measuring electrode is a flat ring through which the active end of a reference electrode projects.

For a regular check on the proper operation of the cathodic protection system, a measurement can be carried out from time to time in the manner described above. However, sometimes it is desirable to continuously monitor the potential so that the average potential over a relatively long period of time, for example a month, can be determined.

SUMMARY OF THE INVENTION

Therefore, the present invention provides arrangement for continuously monitoring over a long period of time, the potential on a buried cathodically protected metallic structure.

The measured potential is continuously compared with a set reference potential by a comparison circuit during a measuring time cycle. The amount by which the measured potential is higher than the reference potential is converted into a pulse stream signal, the frequency of pulses of which is proportional to the magnitude of this difference. The number of pulses occurring during the measuring time cycle is counted by a pulse counter. The time interval between the start and end of a measuring cycle is recorded. After the measuring cycle the average value of the amount by which the measured potential has been higher than the reference potential during the measuring cycle is determined by computation from the number of pulses counted by the pulse counter and the recorded time interval over which those pulses were counted.

The average value is representative of the extent to which the cathodic protection may not have been adequate during the measuring cycle, and hence of the corrosion effects to be expected. During the periods within the measuring cycle when the measured potential is lower than the reference potential, the protection is considered to be adequate and no pulsed signal is fed to the pulse counter. The time interval between the start and end of a measuring time cycle can be predetermined and may for example amount to any value between 1 day and 1 year. A measuring cycle of of about 1 month has been found to be very suitable in practice. The time interval is preferably recorded by means of a digital clock.

Thus, the present invention provides a method for the long term monitoring of the potential with respect to the soil of a metallic structure situated in the soil and cathodically protected by an externally applied DC voltage, comprising the steps of: inserting a measuring electrode into the soil adjacent to the structure to be monitored; placing a reference electrode in the soil; electrically connecting the measuring electrode to the structure; generating a reference potential; measuring the potential difference between the measuring and reference electrodes; comparing the measured potential difference with the reference potential and generating a comparison signal indicative of the amount by which the measured potential exceeds the reference potential; generating a pulse signal having a pulse frequency proportional to the magnitude of the comparison signal so that the frequency is proportional to the amount by which the measured potential exceeds the reference potential; counting the number of pulses of the pulse signal during a measuring cycle; determining and recording a time interval of the measuring cycle; and computing, after completing the measuring cycle, the average value of the amount by which the measured potential exceeds the reference potential during the measuring time cycle.

The invention also provides an apparatus for monitoring the potential with respect to the soil of a metallic structure buried in the soil and cathodically protected by means of an applied DC voltage. The apparatus includes a measuring electrode to be inserted into the soil near the cathodically protected structure and connected electrically with this structure, a reference electrode placed in or near this measuring electrode in or on the soil, and a measuring circuit for measuring the potential difference between the measuring electrode and the reference electrode.

The measuring circuit is provided with a reference stage for the adjustable generation of a reference potential, a comparison stage for the continuous generation during a measuring cycle of a difference signal corresponding to the amount by which the measured potential is higher than the reference potential, a voltage-frequency converter for converting the difference signal into a pulsed signal the frequency of which is proportional to the said amount, a pulse counter for counting the number of pulses during the measuring time cycle and means for recording the time interval between the start and end of a measuring cycle.

The measuring circuit is preferably provided with a computer stage with the aid of which the average value of the amount by which the measured potential has been higher than the reference potential during the measuring cycle can be calculated from the number of pulses counted in the pulse counter and the recorded time interval. The means for recording the time interval consists preferably of a digital clock. A digital display is preferably used for reading out the number of pulses counted during a measuring cycle, the recorded time interval or the calculated value.

Thus, the present invention also provides an apparatus for monitoring the potential with respect to the soil of a metallic structure buried in soil and cathodically protected by an externally applied DC voltage, comprising: a measuring electrode for placement in the soil adjacent to the structure to be monitored, the electrode being electrically connected to the structure; a reference electrode placed on or in the soil; a measuring circuit coupled to the measuring and reference electrodes for measuring the potential difference between the measuring and reference electrodes, the measuring circuit including a generator for generating a reference potential; a comparator for comparing the measured potential difference between the measuring electrode and the reference electrode with the reference potential and providing a comparison signal indicative of the amount by which the measured potential difference exceeds the reference potential; a pulse signal generator, for generating, in response to the comparison signal, a pulse stream signal having a pulse frequency proportional to the comparison signal and therefore proportional to the amount by which the measured potential difference exceeds the reference potential; a counter for connecting the number of pulses of the pulse stream signal during a measuring cycle; timer means for determining and recording the time interval of the measuring cycle; and means, coupled to the counter and timer means so as to receive data therefrom, for computing, after completion of the measuring cycle, the average value of the amount by which the measured potential has been higher than the reference potential during the measuring cycle.

BRIEF DESCRIPTION OF THE DRAWINGS

The invention will be explained with reference to the following Figures wherein like reference numerals designate like or corresponding parts or elements.

DETAILED DESCRIPTION OF THE PREFERRED EMBODIMENT

Figure 1:
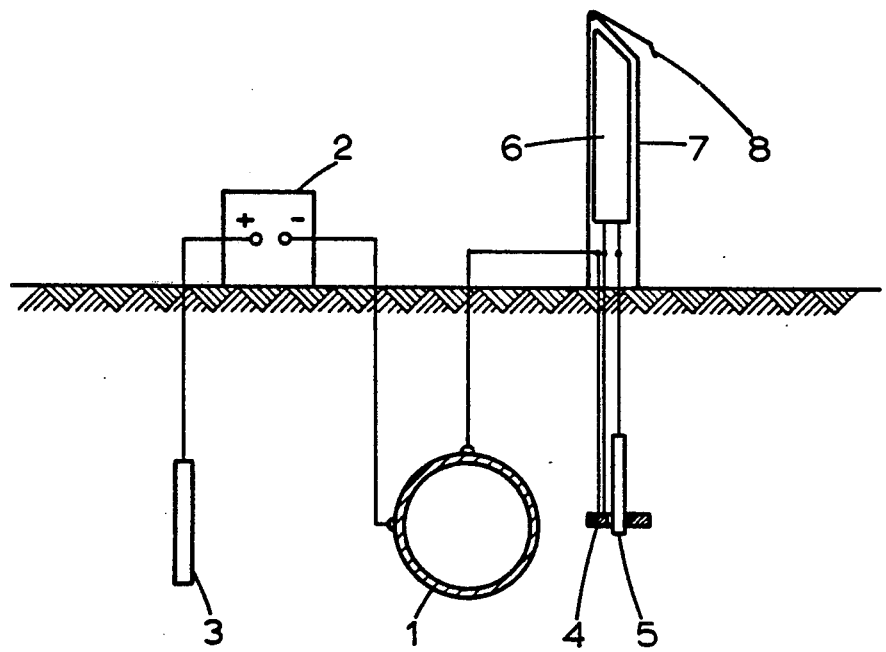
FIG. 1 is a schematic view of a device according to the invention, for use in measuring a cathodically protected underground pipeline.

Referring now to FIG. 1, there is shown an underground steel pipeline 1. The pipeline 1 is cathodically protected by an installation 2, which provides the pipeline with a negative voltage with respect to the in situ anode 3 in the soil. In order to monitor the proper operation of the cathodic protection continuously, use is made of a device consisting of an annular measuring electrode 4, a reference electrode 5 the active end of which projects through the opening of measuring electrode 4 and a measuring circuit 6 which is housed in a permanent measuring column 7. Another arrangement of electrode 4 and 5 with respect to one another or another form of the electrodes can also be used without departing from the spirit of the present invention. Measuring column 7 is provided with a cover 8 which can be locked. Measuring electrode 4 is connected to both the measuring circuit 6 and to the pipeline 1.

Figure 2:
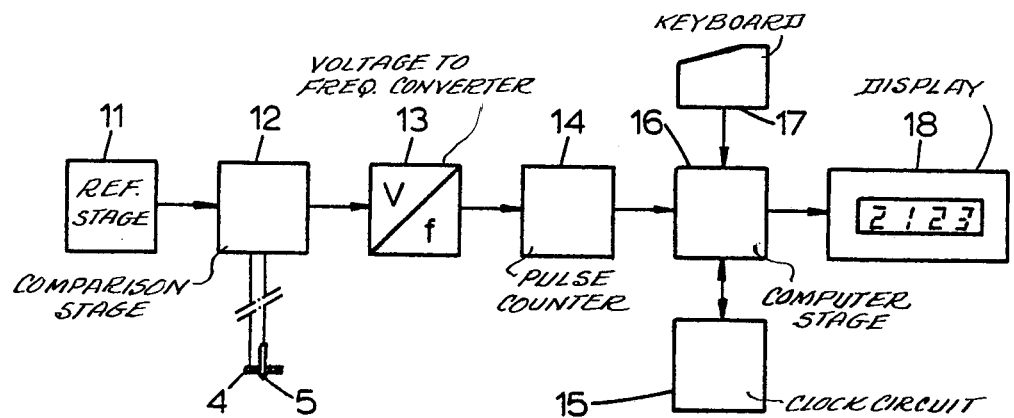
FIG. 2 is a block diagram of the measuring circuit associated with the device shown in FIG. 1.

Referring now to FIG. 2, there is shown a block diagram of measuring circuit 6 and its interconnection with electrodes 4 and 5. A reference stage 11 generates a reference potential. A comparison stage 12 compares the measured potential with the reference potential established by reference stage 11 and generates an output signal indicative of the amount by which the measured potential is higher than the reference potential. If the measured potential is lower than the reference potential, the output signal of the comparison stage 12 is zero. The output signal of the comparison stage 12 is converted by a voltage-frequency converter 13 into a pulse stream signal the frequency of pulses of which is proportional to the output signal of the comparison stage 12. The voltage-frequency converter 13 delivers no pulses if the measured potential is lower than the reference potential.

The pulses generated by the voltage-frequency converter 13 are counted by a pulse counter 14 during a time interval running from the start to the end of a measuring cycle. The measuring cycle time interval is recorded with the aid of a digital clock circuit 15. A computer stage 16 calculates from the number of pulses counted in pulse counter 14 during a measuring cycle and the time recorded by clock 15, the average value of the amount by which the measured potential has been higher than the reference potential during a measuring cycle. A keyboard 17 is associated with computer stage 16. Keyboard 17 can be used to enter commands such as those required for (a) resetting pulse counter 14 to zero before the start of a measuring cycle, (b) recording the start time in clock circuit 15, (c) starting the measuring cycle, (d) stopping the measuring cycle after a predetermined interval of time such as for example one (1) month, and (e) controlling the calculation of a result based upon data supplied by the counter and clock and the display of that result by a display 18. The details of reference stage 11 and comparison stage 12, are set forth in FIG. 3.

Figure 3:
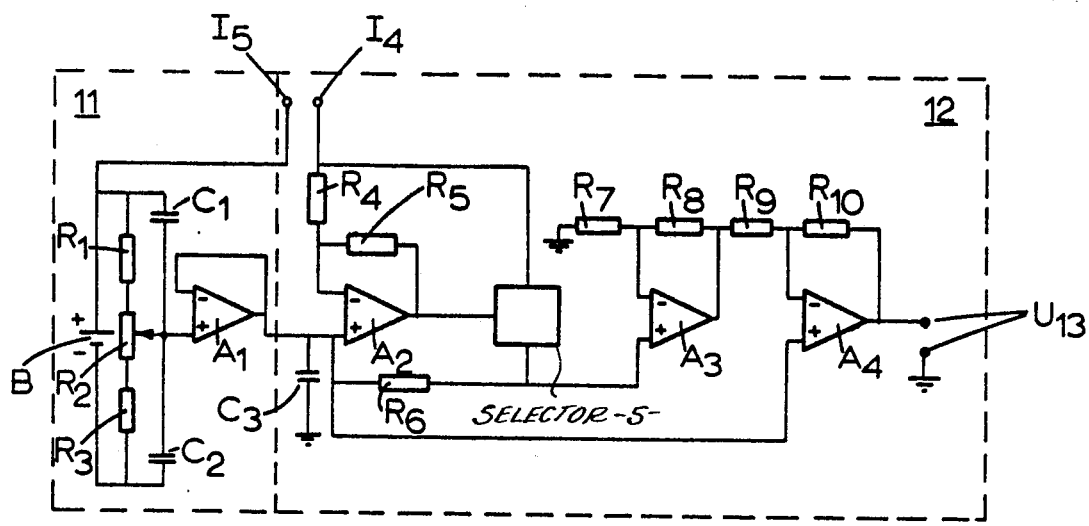
FIG. 3 is a schematic diagram of reference stage 11 and the comparison stage 12 of the measuring circuit shown in FIG. 2.

Referring now to FIG. 3, reference stage 11 comprises a DC voltage source B from which is derived a comparison potential via a variable voltage divider circuit including fixed resistors R1 and R3 and potentiometer R2. This comparison potential is fed via an operational amplifier A1 connected in circuit as a voltage-follower to comparison stage 12. Measuring electrode 4 is connected to a contact I4 and reference electrode 5 is connected to a contact I5. In comparison stage 12, an operational amplifier A2, a selector S and resistances R4—R5—R6 form a discriminator circuit which passes either the comparison potential, or the measured potential via input I4, to the non-inverting input of operational amplifier A3. The potential passed by the discriminator is the higher of these two potentials.

The comparison potential is applied to the non-inverting input of an operational amplifier A4. Operational amplifiers A3 and A4 form, together with four equal resistances R7, R8, R9 and R10, a difference circuit. The output signal appearing at an output U13 of this difference circuit is proportional to the difference between the potentials at the noninverting inputs of operational amplifiers A3 and A4. If the comparison potential is higher than the measured potential, this difference is zero (A3 and A4 each have the comparison potential at their non-inverting inputs). If the measured potential is higher than the comparison potential, a signal proportional to the difference is passed via output U13 to the voltage-frequency converter 13.

In the specific circuit shown in FIG. 3, the operational amplifiers A1–A4, the selector S and the voltage-frequency converter 13 are all commercially available solid-state elements. The use of decoupling capacitors C1, C2 and C3 as shown in the figure is recommended.

Referring again to FIG. 2, components 14 to 18 are shown as discrete block components. However, in a practical embodiment, these components may be obtained in the form of a commercially available calculator with digital clock, which can be modified as necessary by one of ordinary skill in the art.

The drawing shows only those parts necessary for a clear understanding of the invention. Other essential elements such as the power supply, an RC circuit which determines the voltage-frequency proportionality of the V-f converter etc. are not shown because they can be easily added by one of ordinary skill in the art.

For a regular check on the operation of the cathodic protection, an operator visits all measuring columns along a pipeline periodically, for example once a month, reads the data collected during the past period, replaces batteries if necessary, checks the installation (in particular the reference potential) and starts a new measuring cycle. The duration of the measuring cycle can be easily adapted to meet specific measuring requirements such as a more or less frequent check than once a month.

While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

I claim:

1. An apparatus for monitoring the potential with respect to the soil of a metallic structure buried in soil and cathodically protected by an externally applied DC voltage, comprising:
   a measuring electrode for placement in the soil adjacent to the structure to be monitored, the electrode being electrically connected to the structure;
   a reference electrode placed on or in the soil;
   a measuring circuit coupled to the measuring and reference electrodes for measuring the potential difference between the measuring and reference electrodes, the measuring circuit including
   a generator for generating a reference potential;
   a comparator for comparing the measured potential difference between the measuring electrode and the reference electrode with the reference potential and providing a comparison signal indicative of the amount by which the measured potential difference exceeds the reference potential;
   a pulse signal generator, for generating, in response to the comparison signal, a pulse stream signal having a pulse frequency proportional to the comparison signal and therefore proportional to the amount by which the measured potential difference exceeds the reference potential;
   a counter for counting the number of pulses of the pulse stream signal during a measuring time cycle;
   timer means for determining and recording the time interval of the measuring time cycle; and
   means, coupled to the counter and timer means so as to receive data therefrom, for computing, after completion of the measuring cycle, the average value of the amount by which the measured potential has been higher than the reference potential during the measuring time cycle.

2. An apparatus according to claim 1, wherein the time interval of the measuring cycle is between 1 day and 1 year.

3. An apparatus according to claim 1 or 2, wherein the timer means comprises a digital clock.

4. An apparatus for monitoring the potential with respect to the soil of a metallic structure situated in the soil and cathodically protected by an externally applied DC voltage, comprising:
   a measuring electrode for placement in the soil adjacent to the structure to be monitored, the electrode being electrically connected to the structure;
   a reference electrode placed on or in the soil;
   a measuring circuit coupled to the measuring and reference electrodes for measuring the potential difference between the measuring and reference electrodes, the measuring circuit including a reference stage for generating a fixed but adjustable reference potential, a comparison stage for continuously generating, during a measuring cycle, a difference signal indicative of the amount by which the measured potential difference is higher than the reference potential generated by the reference stage, a voltage to frequency converter for generating a pulse stream signal, the frequency of which is proportional to the difference signal, a pulse counter for counting a number of pulses provided by the voltage to frequency converter during the measuring cycle, and means for recording the time interval between the start and end of the measuring cycle.

5. An apparatus according to claim 4, wherein the measuring circuit comprises a computer stage for determining the average value of the amount by which the measured potential has been higher than the reference potential during the measuring cycle from the number of pulses counted in the pulse counter and the recorded time interval.

6. An apparatus according to claim 5, wherein the pulse counter and the computer stage are constructed as a single unit.

7. An apparatus according to claim 4 or 5 or 6, wherein the means for recording a time interval comprises a digital clock.

8. An apparatus according to claim 4 or 5 or 6, further comprising a digital display for displaying any of (a) the number of pulses counted during a measuring cycle, (b) the recorded time interval and (c) the calculated average value.

9. An apparatus according to claim 7, further comprising a digital display for displaying any of (a) the number of pulses counted during a measuring cycle, (b) the recorded time interval and (c) the calculated average value.

10. An apparatus according to claim 4 or 5 or 6, wherein the reference stage of the measuring circuit comprises a DC voltage source, an adjustable potentiometer circuit and a first operational amplifier connected as voltage-follower, and wherein the comparison stage of the measuring circuit comprises a solid-stage selector and a second, a third and a fourth operational amplifier, the second operational amplifier being combined with the selector to form a discriminator circuit at the output of which either the set comparison potential or the potential of the measuring electrode appears, the potential appearing being the higher of the two potentials, the third and fourth operational amplifiers being combined to form a difference circuit to which the comparison potential and the output potential of the discriminator circuit are fed, and at the output of which a voltage difference appears which is proportional to the difference of these two potentials.

11. An apparatus according to claim 7, wherein the reference stage of the measuring circuit comprises a DC voltage source, an adjustable potentiometer circuit and a first operational amplifier connected as voltage-follower, and wherein the comparison stage of the measuring circuit comprises a solid-stage selector and a second, a third and a fourth operational amplifier, the second operational amplifier being combined with the selector to form a discriminator circuit at the output of which either the set comparison potential or the potential of the measuring electrode appears, the potential appearing being the higher of the two potentials, and the third and fourth operational amplifiers being combined to form a difference circuit to which the comparison potential and the output potential of the discriminator circuit are fed, and at the output of which a voltage difference appears which is proportional to the difference of these two potentials.

12. An apparatus according to claim 8, wherein the reference stage of the measuring circuit comprises a DC voltage source, an adjustable potentiometer circuit and a first operational amplifier connected as voltage-follower, and wherein the comparison stage of the measuring circuit comprises a solid-stage selector and a second, a third and a fourth operational amplifier, the second operational amplifier being combined with the selector to form a discriminator circuit at the output of which either the set comparison potential or the potential of the measuring electrode appears, the potential appearing being the higher of the two potentials, and the third and fourth operational amplifiers being combined to form a difference circuit to which the comparison potential and the output potential of the discriminator circuit are fed, and at the output of which a voltage difference appears which is proportional to the difference of these two potentials.

13. A method for the long term monitoring of the potential with respect to the soil of a metallic structure situated in the soil and cathodically protected by an externally applied DC voltage, comprising the steps of:
inserting a measuring electrode into the soil adjacent to the structure to be monitored;
placing a reference electrode in the soil;
electrically connecting the measuring electrode to the structure;
generating a reference potential;
measuring the potential difference between the measuring and reference electrodes;
comparing the measured potential difference with the reference potential and generating a comparison signal indicative of the amount by which the measured potential exceeds the reference potential;
generating a pulse signal having a pulse frequency proportional to the magnitude of the comparison signal so that the frequency is proportional to the amount by which the measured potential exceeds the reference potential;
counting the number of pulses of the pulse signal during a measuring cycle;
determining and recording a time interval of the measuring cycle; and
computing, after completing the measuring cycle, the average value of the amount by which the measured potential exceeds the reference potential during the measuring cycle.

14. A method according to claim 13 wherein the time interval of the measuring cycle is between 1 day and 1 year.

* * * * *

UNITED STATES PATENT AND TRADEMARK OFFICE
CERTIFICATE OF CORRECTION

PATENT NO. : 4,437,065
DATED : March 13, 1984
INVENTOR(S) : Gerrit Woudstra

It is certified that error appears in the above-identified patent and that said Letters Patent is hereby corrected as shown below:

On the title page assignee should read:

-- (73) Assignee: N.V. Nederlandse Gasunie, Groningen, Netherlands --.

Signed and Sealed this

Fourteenth Day of August 1984

[SEAL]

Attest:

GERALD J. MOSSINGHOFF

Attesting Officer      Commissioner of Patents and Trademarks